United States Patent [19]

Ohasi et al.

[11] Patent Number: 4,840,970

[45] Date of Patent: Jun. 20, 1989

[54] AQUEOUS SOLUTION CONTAINING LIPID-SOLUBLE PHARMACEUTICAL SUBSTANCE

[75] Inventors: Hiroyuki Ohasi; Toru Takami, both of Kanagawa; Noritoshi Koyama, Saitama; Yoshio Kogure, Saitama; Katsumi Ida, Saitama; Kazumi Iijima, Gumma; Tomohiro Kobori, Saitama, all of Japan

[73] Assignee: Eisai Co., Ltd., Tokyo, Japan

[21] Appl. No.: 56,302

[22] Filed: Jun. 1, 1987

Related U.S. Application Data

[63] Continuation of Ser. No. 634,113, Jul. 24, 1984, abandoned.

[30] Foreign Application Priority Data

Jul. 25, 1983 [JP] Japan ................... 58-134260

[51] Int. Cl.$^4$ ............ A61K 31/12; A61K 31/07; A61K 31/335; A61K 31/225
[52] U.S. Cl. .................... 514/690; 514/458; 514/548; 514/681; 514/725; 514/775
[58] Field of Search ........... 514/167, 168, 458, 690, 514/725, 775, 548, 681

[56] References Cited

U.S. PATENT DOCUMENTS

| | | | |
|---|---|---|---|
| 2,709,149 | 5/1955 | Dunmire | 424/81 |
| 3,143,475 | 8/1964 | Koff | 424/236 |
| 3,773,930 | 11/1973 | Mohammed et al. | 424/237 |

OTHER PUBLICATIONS

Chem. Abst. 102:225858(k)(1985)—Tutsky.
Chem. Abst. 102:32312(n)(1985)—Wexler et al.
Chem. Abst. 101:137044(r)(1984)—Bilton.
Chem. Abst. 100:145017(d)(1984)—Eisai Co. Ltd.
Chem. Abst. 99:193488(r)(1983)—Q. P. Corp.
Chem. Abst. 99:110773(f)(1983)—Ohashi et al.
Chem. Abst. 98:8191(g)(1983)—Nippon Shinyaku Co. Ltd.
Chem. Abst. 97:54597w(1982)—Eisa: Co. Ltd.

*Primary Examiner*—Douglas W. Robinson
*Assistant Examiner*—Z. Fay
*Attorney, Agent, or Firm*—Wenderoth, Lind & Ponack

[57] ABSTRACT

Disclosed herein is an aqueous solution containing a lipid-soluble active vitamin substance and/or ubiquinone. The solution has a pH of 5.5–8 and additionally contains a hydrogenated lecithin and neutral amino acid. It is stable and free from side effects, and is rather easy to prepare.

9 Claims, No Drawings

4,840,970

AQUEOUS SOLUTION CONTAINING LIPID-SOLUBLE PHARMACEUTICAL SUBSTANCE

This application is a continuation of application Ser. No. 634,113 filed July 24, 1984, now abandoned.

BACKGROUND OF THE INVENTION (1) Field of the Invention:

This invention relates to an improvement in an aqueous solution which contains a lipid-soluble pharmaceutical substance, namely, a lipid-soluble active vitamin substance and/or ubiquinone.

By the term "lipid-soluble active vitamin substance" is meant one or more substances selected from the group consisting of lipid-soluble sources of vitamin A, lipid-soluble sources of vitamin E and lipid-soluble sources of vitamin K.

(2) Description of the Prior Art:

Vitamin A has been known as a substance important for the promotion of growth, visual function and reproduction. It is recently attracting attention for its reported carcinostatic activities. On the other hand, vitamin E and vitamin K have been finding wide-spread clinical utility respectively owing to the biochemical anti-oxidation and biomembrane stabilization effects and as a substance pertaining to blood clotting and the electron transport system. These vitamins are these days desired to be available as aqueous solutions.

On the other hand, the term "ubiquinone" as used herein may embrace a variety of substances which individually contain different numbers of isoprene moieties in their structures. All of these ubiquinone substances have already been found effective substances in view of their physiological activities or effects such as supply of energy for cell activities, anti-oxidation effects, immune reinforcement reaction and aldosterone antagonism. Among such ubiquinone substances, a ubiquinone substance which is generally called ubidecarenone or $CoQ_{10}$ and contains 10 isoprene moieties has been formed into pharmaceutical preparations.

Reflecting on finding of such pharmaceutical substances which are applicable in a yet broader field in recent years, a new desire has arisen for the availability of such pharmaceutical substances as aqueous solutions rather than as solid forms.

As a method for solubilizing the above-mentioned lipidsoluble active vitamin substance and or ubiquinone, there is a conventional technique which makes use of a non-ionic surfactant, for example, HCO-60 (trade name; product of Nikko Chemical Co., Ltd., Japan). This prior art method however requires a great deal of HCO-60. As a result, the thus-prepared aqueous solution is susceptible of liberating histamine-like substances due to HCO-60 when administered as an injectable preparation, or when administered as an orally-dosable preparation, creates problems in the intestinal tract and thus brings about undesirable side effects such as diarrhea.

It has also been known to employ lecithin as an emulsifier. However, lecithin has weak emulsification capacity only. Therefore, this method requires a special apparatus called "pressure homogenizer". Moreover, the long-term stability of each resulting emulsion is not considered to be sufficient, thereby requiring such an additive as vegetable oil or ethanol (see, Japanese Patent Application Laid-open No. 56315/1978).

Accordingly, the present inventors developed techniques both featuring an incorporation of a hydrogenated lecithin with a view toward providing an aqueous solution which contains a lipid-soluble active vitamin substance and/or ubiquinone and remains stable over a prolonged period of time without need for the addition of any additive causing potential problems (see, Japanese Patent Application Nos. 209972/1981 and 212695/1982).

Thereafter, the present inventors made a further investigation on such aqueous solutions, resulting in the finding that it is preferable to adjust the pH of such an aqueous solution to 5.5–8. Since the aqueous solution is primarily used as an injectable preparation or orally-dosable preparation for pharmaceutical applications, it is desired to adjust its pH to the physiological pH range of living bodies, namely, to 5.5–8. Thus, additives were freely chosen to adjust the pH level of the above-mentioned aqueous solution. Such additives were incorporated to obtain final products. As a result, the resultant aqueous solutions tended to show some turbidity on visual inspection. When they were subjected to sterilization under suitable conditions, a significant clarity change was observed after the sterilization. Hence, it became necessary to make a search for an additive capable of adjusting the pH to 5.5–8 without developing any significant turbidity by such an adjustment, and a variety of substances were studied, leading to completion of the present invention.

SUMMARY OF THE INVENTION

With the foregoing in view, an object of this invention is to provide an aqueous solution containing a lipid-soluble active vitamin substance and/or ubiquinone which solution is free from the drawbacks of the above-described prior art techniques and has a pH adjusted to 5.5–8 and good stability without need for any additives causing potential problems.

In one aspect of this invention, there is thus provided an aqueous solution containing a lipid-soluble active vitamin substance and/or ubiquinone, the improvement wherein the solution further comprises hydrogenated lecithin and a neutral amino acid incorporated therein and the pH of the solution ranges from 5.5 to 8.

The aqueous solution according to this invention has remarkable advantageous effects in that it is stable and does not induce side effects.

The above and other objects, features and advantages of the present invention will become apparent from the following description and the appended claims.

DETAILED DESCRIPTION OF THE INVENTION

Briefly speaking, the present invention relates to an aqueous solution containing a lipid-soluble active vitamin substance and/or ubiquinone, which solution features an incorporation of a hydrogenated lecithin and neutral amino acid and a pH in the range of 5.5–8.

It is the principal feature of the aqueous solution according to this invention that when it is subjected to steam sterilization at a pH of 5.5–8, at 100° C. and for 1 hour, its transmittance $T_{640}$ is measured at 640 nm both before and after the sterilization and its percent change in transmittance (%) defined by the following equation is calculated, the percent change in transmittance is small.

$$\text{Percent change in transmittance} (\%) = \frac{T_{640} \text{ (before sterilization)} - T_{640} \text{ (after sterilization)}}{T_{640} \text{ (before sterilization)}} \times 100$$

Therefore, the present invention provides an aqueous solution containing a lipid-soluble active vitamin substance and/or ubiquinone and having a small percent change in transmittance owing to a novel combination of constituent elements in this invention, which constituent elements will hereinafter be described specifically. The present invention will hereinafter be described more specifically.

As has already mentioned, the term "lipid-soluble active vitamin substance" as used herein means one or more substances selected from the group consisting of lipid-soluble active vitamin A substances, lipid-soluble active vitamin E substances and lipid-soluble active vitamin K substances.

As exemplary lipid-soluble active vitamin A substances useful in the practice of this invention, may be mentioned vitamin A per se and its esters, for example, vitamin A pulmitate. Illustrative of the lipid-soluble active vitamin E substance are vitamin E per se and its esters, for instance, vitamin E acetate and vitamin E nicotinate in the present invention. On the other hand, vitamins $K_1$-$K_3$, their dihydrogen derivatives and demethyl derivatives may be mentioned as exemplary lipid-soluble active vitamin K substances useful in the practice of this invention.

A variety of ubiquinones may be used in the present invention, among which ubidecarenone ($CoQ_{10}$) is preferred.

On the other hand, the term "hydrogenated lecithin" as used herein means a lecithin the anti-oxidation property of which has been enhanced by its hydrogenation. More specifically, exemplary hydrogenated lecithins may embrace hydrogenated soybean lecithin, hydrogenated ovolecithin and the like with hydrogenated soybean lecithin being particularly preferred It is preferred that each of these hydrogenated lecithins contains at least 85% of a phospholipid component and has an iodine value of 10-60, notably 25-50. These iodine value ranges have been determined, because any iodine values smaller than 10 lead to lecithins, which have by themselves been hardened to a considerable degrees and hence render their actual coarse dispersions difficult, whereas any iodine values in excess of 60 are not expected to bring about the advantageous effects of this invention. The hydrogenated lecithin may preferably contain, as the phospholipid component, phosphatidyl choline at a high level. In the case of a soybean phospholipid component for example, it may contain 80-95% of phosphatidyl choline Besides, lysolechithin and phosphatidyl ethanolamine may also be detected Particularly preferred hydrogenated lecithins are those recited in Japanese Patent Application Laid-open Nos. 83911/1977 and 62010/1980.

In the aqueous solution of this invention, the lipid-soluble active vitamin substance and/or ubiqunione and the hydrogenated lecithin may be contained in the following amounts.

First of all, the concentration of a lipid-soluble active vitamin and/or ubiquinone in an aqueous solution is required to be 0.1-1.0% from the clinical viewpoint. Concentrations in the range of 0.2-0.5% are popularly employed for usual applications A concentration of 0.2% or so is often used especially when such aqueous solutions are used as injectable preparations. It should however be borne in mind that the concentration of the lipid-soluble active vitamin and/or ubiquinone is not necessarily limited to the above range.

The hydrogenated lecithin may be incorporated at various different concentration levels in accordance with what end use would be made on the resulting aqueous solutions. When an aqueous solution is desired to be clear in view of its application, it is preferred to add the hydrogenated lecithin in an amount of 1-5 parts by weight per part by weight of the lipid-soluble active vitamin substance and/or ubiquinone. Where slight cloudiness is tolerated for an aqueous solution, the hydrogenated lecithin may be incorporated from as little as 0.1-1 parts by weight to as much as 5-15 parts by weight, both, per part by weight of the lipid-soluble active vitamin substance and/or ubiquinone. For practical purposes, the hydrogenated lecithin may be added in an amount of 0.1-15 parts by weight per part by weight of the lipid-soluble active vitamin substance and/or ubiquinone. However, it is not necessary to limit the concentration of the hydrogenated lecithin to the above-mentioned ranges in the present invention.

In the aqueous solution of this invention, a part of water may be replaced by a water-miscible solvent such as ethanol, propylene glycol, a low molecular weight polyethylene glycol, glycerin or the like. These solvents are effective in shortening to a considerable extent the time required to disperse coarsely and evenly the lipid-soluble active vitamin substance and/orubiquinone in the first step upon preparation of the aqueous solution. Namely, the time required for the solubilization of the lipid-soluble active vitamin substance and/or ubiquinone may be shortened when the lipid-soluble active vitamin substance and/or ubiquinone is in advance dispersed coarsely in the water-miscible solvent in the presence of the hydrogenated lecithin instead of mixing the lipid-soluble active vitamin substance and/or ubiquinone directly with the hydrogenated lecithin and then adding water to the resultant mixture. It should however be borne in mind that the water-miscible solvent may be used to facilitate the preparation of the aqueous solution of this invention and the object of this invention can thus still be attained without incorporation of such a water-miscible solvent.

Therefore, it is not essential for the present invention to add such a solvent.

If the water-miscible solvent is added in order to facilitate the preparation of the aqueous solution of this invention, it may be incorporated in an amount of 1-50 parts by weight per part by weight of the lipid-soluble active vitamin substance and/ or ubiquinone and in an amount of 2-10 wt./vol. % of the aqueous solution of this invention.

When the aqueous solution of this invention is used as an injectable preparation, it is possible to add a sugar and/or sugar alcohol such as glucose, xylitol, sorbitol, mannitol and/or the like, which are commonly and widely used as isotonizing agents in injectable preparations. Namely, addition of these isotonizing agents are effective in avoiding occurrence of a haze or the like upon sterilization of injectable preparations without deleteriously affecting the meritorious features of this invention. It is preferred to add such an isotonizing agent in an amount of 1-10% of the aqueous solution of this invention.

Next, the term "neutral amino acid" as used herein means an amino-containing acid, an aqueous solution of which has a pH in the neutral range. As its specific and representative examples, there may be mentioned glycine, alanine, β-alanine, serine, threonine, valine, isoleucine, leucine, phenylalanine, methionine, histidine and taurine. These amino acids may be used either singly or in combination.

Since the pH of an aqueous solution of each of these neutral amino acids falls within the neutral range, the neutral amino acid can adjust the pH of the aqueous solution of this invention to 5.5 to 8. In some instances, they may show buffer actions at the pH level. It has however been unknown to date that at the same time, they serve to keep the percent change in transmittance of the aqueous solution of this invention at a small value.

It is preferred to limit the concentration of such a neutral amino acid to 0.05–6 wt./vol. % in the aqueous solution of this invention. Needless to say, it is not essential to limit the concentration of the neutral amino acid to the above range.

The pH of the aqueous solution of this invention is limited to 5.5–8. This limitation to the pH range is an essential requirement for the aqueous solution of this invention in view of its physiological application. Such a pH range can be achieved by incorporating one or more of the neutral amino acids and if necessary, adding an acidic or alkaline substance to make a fine pH adjustment.

The aqueous solution of this invention may be prepared in a manner to be outlined hereinbelow. First of all, a small amount of water is added to the lipid-soluble active vitamin substance and/or ubiquinone and the hydrogenated lecithin. Thereafter, the resulting mixture is coarsely and evenly dispersed preferably while heating it at 60°–70° C. For the sake of efficient dispersion, it is preferred to apply a pressure or ultrasonic waves while agitating the mixture, so that the mixture is forced to disperse. The coarse dispersion may be facilitated further when a water-miscible solvent such as ethanol, propylene glycol, a low molecular weight polyethylene glycol, glycerin or the like is used in lieu of a part of water. Then, the neutral amino acid, other components and the remaining water are added to the thus-obtained coarse dispersion and the resulting mixture is dispersed evenly, leading to the provision of the aqueous solution of this invention. When using the aqueous solution of this invention as an injectable preparation, it is necessary to filter the aqueous solution, fill the thus-filtered aqueous solution in desired ampules and sterilize it in the ampules. Incidentally, a pharmaceutically-acceptable germicide, isotonizing agent and/or the like may also be chosen at will as other materials to be incorporated. However, it is preferable to avoid addition of any electrolytic component because it hinders the dispersion, especially the solubilization.

By the way, the hydrogenated lecithin may be prepared by charging lecithin in an autoclave, adding a solvent and catalyst into the autoclave, and then causing the hydrogenation of the lecithin to proceed to a desired iodine value while maintaining the reaction mixture in contact with hydrogen. After completion of the reaction, the catalyst is filtered off and the solvent is then distilled off to obtain the hydrogenated lecithin.

As the hydrogenated lecithin useful in the practice of this invention, it is particularly preferred to use a specially-purified hydrogenated lecithin such as that disclosed in Japanese Patent Application Laid-open No. 2010/1980 which was referred to in the above.

The present invention will hereinafter be described in further detail in the following Examples, which will be given by way of example only and not by way of limitation of the invention.

EXAMPLE 1

Added to vitamin $K_2$ (500 mg) were hydrogenated soybean lecithin (500 mg), propylene glycol (4 g) and water (20 ml). The resulting mixture was stirred with heating and was then subjected to an ultrasonic processing (20 KHz, 200 W) for 120 minutes in an nitrogen-substituted atmosphere to obtain an aqueous solution. Sorbitol (5 g) and the remaining water were added to the thus-prepared aqueous solution to make the total volume be 90 ml, followed by dissolution of proline (1 g). The pH of the resulting aqueous mixture was adjusted to 7.0 with an aqueous solution of sodium hydroxide. Then, water was added in such an amount that the total volume of the resulting mixture was increased to 100 ml. The thus-obtained aqueous solution was filtered by a membrane filter, purged with nitrogen gas, and filled in brown ampules. The ampules were melt-sealed and were then sterilized at 115° C. for 30 minutes to obtain stable injectable preparations which contained vitamin $K_2$.

EXAMPLE 2

Hydrogenated and purified ovolecithin (250 mg), glycerin (3 g) and water (30 mg) were added to vitamin E nicotinate (200 mg). The resulting mixture was agitated with heating, and was then stirred for 50 minutes in a nitrogen-substituted atmosphere by a high-speed stirrer to obtain an aqueous solution. Then, sorbitol (20 g), methylparaben (100 mg), orange essence and glycine (500 mg) were added to the aqueous solution, followed by an adjustment of the pH of the resulting mixture to 7.0 with an aqueous solution of sodium hydroxide. Thus, a stable syrup containing vitamin E nicotinate (100 ml in total) was obtained.

No significant change was observed in the transmittance ($T_{640}$) of the syrup even after it had been allowed to stand at room temperature for 1 month.

EXAMPLE 3

Added to free vitamin E (500 mg), were hydrogenated and purified soybean lecithin (2 g), purified sesame oil (500 mg), propylene glycol (6 g) as a solubilizing additive and water (30 ml). The resulting mixture was stirred with heating, and was then stirred in a nitrogen-substituted atmosphere for 90 minutes by a high-speed stirrer to obtain an aqueous solution. Sorbitol (5 g) and serine (500 mg) were added to the aqueous solution. The pH and total volume of the resulting mixture were adjusted respectively to 6.5 and 100 ml with an aqueous solution of sodium hydroxide. Thereafter, the procedures of Example 1 were repeated in much the same way to obtain a stable injectable preparation which contained free vitamin E.

EXAMPLE 4

Hydrogenated and purified soybean lecithin (300 mg), propylene glycol (3 g) as a solubilizing additive and water (30 mg) were added to vitamin A pulmitate (200 mg). The resulting mixture was stirred with heating. It was processed for 60 minutes in a nitrogen-substituted atmosphere by means of a high-speed stirrer to obtain an aqueous solution. Then, xylitol (3 g), ethanol (10 g) and serine (300 mg) were added to the aqueous solution. The pH and total volume of the resulting mixture were adjusted respectively to 6.5 and 100 ml with an aqueous solution of sodium hydroxide to obtain a stable solution suitable for endermic applications and containing vitamin A pulmitate.

No significant change was observed in the transmittance ($T_{649}$) of the solution even after it had been allowed to stand at room temperature for 1 month.

EXAMPLE 5

Water (4 ml) was added to a mixture of ubidecarenone (300 mg), hydrogenated and purified soybean lecithin (400 mg) and sorbitol (4 g). In a nitrogen-substituted atmosphere, the resulting mixture was subjected for 5 minutes to an ultrasonic processing, followed by further addition of water (20 ml) and propylene glycol (4 g). The ultrasonic processing was carried out for 10 minutes to obtain a clear aqueous solution. The rest of the water was added to the aqueous solution to increase its total volume to 90 ml, followed by an addition of alanine (300 mg). The pH of the resulting mixture was adjusted to 6.5 with an aqueous solution of sodium hydroxide. Water was then added to the resulting solution to make its total volume be 100 ml. Thereafter, the procedures of Example 1 were followed in much the same way to obtain a stable injectable preparation which contained ubidecarenone.

The advantageous effects of this invention will hereinafter be described in the following Experiments, in comparison with some comparative examples.

EXPERIMENT 1

Hydrogenated and purified soybean lecithin (220 mg), propylene glycol (3 g) as a solubilizing additive and water (20 ml) were added to ubidecarenone (250 mg). The resulting mixture was stirred with heating. Then, it was subjected for 90 minutes to an ultrasonic processing (20 KHz, 200 W) in a nitrogen-substituted atmosphere to obtain an aqueous solution. Then, sorbitol (5 g) and the remaining water were added to the resulting mixture to make its total volume be 90 ml. Using the various pH-adjusting agents given in Table 1, aqueous solutions obtained in the above-described manner were respectively subjected to pH-adjustment. The volumes of the resulting aqueous solutions were increased to the prescribed level to obtain aqueous solutions each of which contained 0.25% of ubidecarenone. Each of the resulting sample solutions was filtered through a membrane filter, purged with nitrogen gas, and filled in 2-ml portions in ampules. The ampules were melt-sealed and were then steam-sterilized at 100° C. for 1 hour. Their pH values and transmittance values were measured both before and after the sterilization. Changes in transmittance were calculated on the basis of the transmittance values. Results are summarized in Table 1.

TABLE 1

| pH-Adjusting agent | | Before sterilization | | After sterilization | | |
|---|---|---|---|---|---|---|
| Name | Conc. (%) | pH | $T_{640}$ (%) | pH | $T_{640}$ (%) | Percent change (%) |
| Not added | — | 6.09 | 95.2 | 5.38 | 94.0 | 1.3 |
| Aspartic acid | 0.1 | 7.49 | 91.0 | 7.03 | 61.2 | 32.7 |
| Arginic acid | 0.1 | 7.48 | 90.8 | 7.53 | 55.5 | 38.9 |
| Megrumic acid | 0.1 | 7.48 | 90.2 | 7.14 | 75.0 | 16.9 |
| Citric acid | 0.1 | 7.48 | 79.5 | 7.52 | 37.0 | 53.5 |
| Glutamic acid | 0.1 | 7.47 | 90.6 | 6.93 | 64.6 | 28.7 |
| Glycine | 0.1 | 7.51 | 93.5 | 7.04 | 94.5 | 0 |
| " | 0.1 | 7.07 | 94.4 | 6.64 | 94.0 | 0.4 |
| " | 0.1 | 6.60 | 94.8 | 6.47 | 94.3 | 0.5 |
| " | 0.5 | 7.51 | 93.0 | 7.24 | 92.8 | 0.2 |
| " | 0.5 | 7.00 | 93.5 | 6.76 | 93.2 | 0.3 |
| " | 0.5 | 6.58 | 94.2 | 6.50 | 93.8 | 0.4 |
| Alanine | 0.1 | 7.53 | 95.0 | 7.01 | 94.4 | 0.6 |
| " | 0.1 | 7.08 | 95.0 | 6.68 | 93.5 | 1.6 |
| " | 0.1 | 6.58 | 95.2 | 6.57 | 94.0 | 1.3 |
| " | 0.5 | 7.49 | 93.5 | 7.27 | 92.6 | 1.0 |
| " | 0.5 | 7.00 | 94.0 | 6.75 | 93.5 | 0.5 |
| " | 0.5 | 6.53 | 94.0 | 6.45 | 93.4 | 0.6 |
| Threonine | 0.1 | 7.52 | 94.2 | 6.93 | 94.2 | 0 |
| " | 0.1 | 7.02 | 94.8 | 6.44 | 95.0 | 0 |
| " | 0.1 | 6.51 | 95.0 | 6.42 | 95.3 | 0 |
| " | 0.5 | 7.51 | 92.7 | 7.02 | 92.8 | 0 |
| " | 0.5 | 7.00 | 93.4 | 6.59 | 94.0 | 0 |
| " | 0.5 | 6.50 | 94.8 | 6.19 | 94.3 | 0.5 |
| Serine | 0.1 | 7.49 | 94.3 | 6.85 | 94.6 | 0 |
| " | 0.1 | 6.97 | 94.8 | 6.47 | 94.8 | 0 |
| " | 0.1 | 6.50 | 94.7 | 6.28 | 95.0 | 0 |
| " | 0.5 | 7.50 | 92.3 | 7.17 | 92.7 | 0 |
| " | 0.5 | 7.00 | 93.6 | 6.62 | 94.4 | 0 |
| " | 0.5 | 6.51 | 93.7 | 6.31 | 93.8 | 0 |
| Proline | 0.1 | 7.72 | 93.5 | 7.01 | 93.0 | 0.5 |
| Valine | 0.1 | 7.77 | 92.0 | 7.42 | 92.5 | 0 |
| Isoleucine | 0.1 | 7.86 | 91.5 | 7.58 | 92.0 | 0 |
| Methionine | 0.1 | 7.78 | 91.0 | 7.63 | 92.0 | 0 |
| Phenylalanine | 0.1 | 7.48 | 93.5 | 7.49 | 92.5 | 1.1 |
| Histidine | 0.1 | 7.48 | 95.0 | 7.55 | 93.0 | 2.1 |
| Taurine | 0.1 | 7.79 | 91.0 | 7.68 | 91.0 | 0 |

As apparent from Table 1, the preparation added with no pH-adjusting agent had good apparent stability but its pH was lowered by the sterilization to a level outside the stable range for lecithin. Furthermore, the preparations, the pH levels of which were adjusted with the acidic or basic amino acids developed considerable changes in appearance.

Turning on the other hand to the preparations, the pH levels of which were respectively effected with the neutral amino acids in accordance with this invention, their pH levels ranged from 5.5 to 8 and no substantial changes were observed with respect to their appearance.

EXPERIMENT 2

To either one (250 mg) of ubidecarenone, vitamin E acetate and vitamin $K_1$, were added with heating hydrogenated and purified ovolecithin (220 mg), propylene glycol (5 g) as a solubilizing additive and water (20 ml). The resulting mixture was subjected to an ultrasonic processing for 90 minutes in a nitrogen-substituted atmosphere. Thereafter, its pH was adjusted in much the same way as Example 1 to obtain a sample. The sample was subjected at 100° C. for 1 hour to steam sterilization. Its pH values and transmittance values were measured respectively both before and after the sterilization. A change in transmittance was then calculated on the basis of the transmittance values. Results are given in Table 2.

TABLE 2

| Lipid-soluble pharmaceutical substance | pH-Adjusting agent | Before sterilization | | After sterlization | | Percent change (%) |
| --- | --- | --- | --- | --- | --- | --- |
| | | pH | Transmittance (%) | pH | Transmittance (%) | |
| Ubidecarenone | Not added | 4.17 | 89.3 | 4.34 | 87.8 | 1.7 |
| | Phosphoric acid 0.1% | 7.56 | 87.5 | 7.42 | 78.2 | 10.6 |
| | Glycine 0.1% | 7.54 | 88.3 | 7.22 | 86.5 | 2.0 |
| Vitamin E acetate | Not added | 4.38 | 87.2 | 4.49 | 85.5 | 1.9 |
| | Glutamic acid 0.1% | 7.51 | 86.0 | 6.78 | 75.2 | 12.6 |
| | Serine 0.1% | 7.51 | 86.5 | 7.34 | 84.9 | 1.8 |
| Vitamin $K_1$ | Not added | 4.46 | 88.9 | 4.52 | 85.9 | 3.4 |
| | Aspartic acid 0.1% | 7.51 | 85.9 | 6.79 | 76.8 | 10.6 |
| | Alanine 0.1% | 7.53 | 87.8 | 6.83 | 84.2 | 4.1 |

As clearly envisaged from Table 2 and similar to the preparations making use of hydrogenated and purified soybean lecithin, the preparations the pH levels of which were adjusted respectively with the neutral amino acids in accordance with this invention developed less changes compared with those pH-adjusted using phosphoric acid and the acidic amino acids respectively and were thus aqueous solutions more stable than the latter preparations.

Having now fully described the invention, it will be apparent to one of ordinary skill in the art that many changes and modifications can be made thereto without departing from the spirit or scope of the invention as set forth herein.

What is claimed is:

1. In an aqueous solution containing a lipid-soluble source of one or more of vitamins A, E, K or ubiquinone and hydrogenated lecithin in an amount of 0.1 to 15 parts by weight of said lipid-soluble source of said vitamins or ubiquinone, the improvement wherein the solution further comprises a neutral amino acid selected from the group consisting of glycine, alanine, β-alanine, serine, threonine, valine, isoleucine, leucine, phenylalanine, methionine, histidine and taurine incorporated therein in an amount of 0.05 to 6 wt./vol. % of the aqueous solution to adjust the pH of the solution to a range of from 5.5 to 8.

2. The aqueous solution according to claim 1, wherein the hydrogenated lecithin contains at least 85% of a phospholipid component and has an iodine value of 10-60.

3. The aqueous solution according to claim 2, wherein the hydrogenated lecithin is hydrogenated soybean lecithin or hydrogenated ovolecithin.

4. The aqueous solution according to claim 1, wherein the aqueous solution additionally contains a water-miscible solvent, an isotonizing agent or both and wherein the water-miscible solvent is ethanol, propylene glycol, a low molecular weight polyethylene glycol or glycerin.

5. The aqueous solution according to claim 4, wherein the water-miscible solvent is contained in an amount of 1-50 parts by weight per part by weight of the lipid-soluble source of one or more of vitamins A, E, K or ubiquinone and in an amount of 2-10% of the aqueous solution.

6. The aqueous solution according to claim 4, wherein the isotonizing agent is a sugar or sugar alcohol.

7. The aqueous solution according to claim 6, wherein the isotonizing agent is glucose, xylitol, sorbitol or mannitol.

8. The aqueous solution according to claim 6, wherein the isotonizing agent is contained in an amount of 0.05-6 wt./vol. % of the aqueous solution.

9. An aqueous solution according to claim 1 which consists essentially of said ubiquinone, hydrogenated lecithin and amino acid.

* * * * *